United States Patent [19]
Schwab et al.

[11] Patent Number: 6,130,181
[45] Date of Patent: Oct. 10, 2000

[54] METATHESIS CATALYST, AND ITS PREPARATION AND USE

[75] Inventors: Peter Schwab, Bad Dürkheim; Boris Breitscheidel, Limburgerhof; Ralf Schulz, Speyer; Michael Schulz, Ludwigshafen; Ulrich Müller, Neustadt-Musbach, all of Germany

[73] Assignee: BASF Aktiengesellschaft, Ludwigshafen, Germany

[21] Appl. No.: 09/372,065

[22] Filed: Aug. 11, 1999

[30] Foreign Application Priority Data

Aug. 17, 1998 [DE] Germany .......................... 198 37 203

[51] Int. Cl.[7] ................ B01J 23/00; C07C 6/00
[52] U.S. Cl. ........................ 502/300; 585/646; 585/647
[58] Field of Search .......................... 502/300; 585/646, 585/647

[56] References Cited

U.S. PATENT DOCUMENTS 4,795,734 1/1989 Chauvin et al. ...................... 502/355
5,183,796 2/1993 Knuuttila et al. .................... 502/340
5,898,092 4/1999 Commereuc ......................... 585/647

FOREIGN PATENT DOCUMENTS

| 19640026 | 4/1998 | Germany . |
| 19740895 | 3/1999 | Germany . |
| 19746040 | 4/1999 | Germany . |
| 1105564 | 3/1968 | United Kingdom . |

*Primary Examiner*—Steven P. Griffin
*Assistant Examiner*—Cynthia M Donley
*Attorney, Agent, or Firm*—Keil & Weinkauf

[57] ABSTRACT

A catalyst containing $Re_2O_7$ on an inorganic support, wherein the $Re_2O_7$ component is on the support in the form of $Re_2O_7$ particles having a diameter of <1 nm, the rhenium surface area, determined by $N_2O$ pulse chemisorption, is at least 0.4 m$^2$/g, and the $Re_2O_7$ component is distributed over the support in the form of an outer shell having a maximum thickness of 1.5 mm.

9 Claims, No Drawings

METATHESIS CATALYST, AND ITS PREPARATION AND USE

The invention relates to $Re_2O_7$ metathesis catalysts, to a process for the preparation of these catalysts, and to their use in olefin metathesis reactions.

Metathesis reactions are catalyzed by both homogeneous and heterogeneous catalysts. In industrial metathesis processes, preference is given to heterogeneous catalysts, in particular $Re_2O_7$-containing supported catalysts. The patent literature describes a number of $Re_2O_7$-containing supported catalysts and processes for their preparation. For example, GB-A-1,105,564 describes the preparation of $Re_2O_7$-containing supported catalysts by evaporation of $Re_2O_7$ in a stream of inert gas at between 150° C. and 700° C. followed by deposition of the $Re_2O_7$ from the inert-gas stream onto a support.

U.S. Pat. No. 4,795,734 describes $Re_2O_7$-containing supported catalysts which are prepared by impregnating the pores of an alumina-containing support with a solution of a rhenium component, wherein, after addition of the rhenium-containing impregnation solution, the impregnated support is left to stand at between 0° C. and 80° C. for a period of at least 10 hours under conditions under which the solvent does not evaporate. If the impregnated support is left to stand at temperatures above room temperature, the impregnation is carried out by warming the support and the impregnation solution to the appropriate temperature before the impregnation and maintaining this temperature during the impregnation. After the impregnation and standing, the impregnated support is dried at from 85° C. to 250° C. and activated by heating to from 400 to 1000° C.

The disadvantages of the $Re_2O_7$-containing supported catalysts described in the patent literature with respect to use in metathesis reactions are that these catalysts have inadequate catalytic activities and selectivities for economical performance of the processes and especially have inadequate cycle times and service lives.

Experience has shown that high catalytic activities and selectivities and in particular long cycle times and service lives are achieved with supported catalysts if the active component of a supported catalyst, in the present case $Re_2O_7$, is in very highly disperse form on the support, i.e. the $Re_2O_7$ particles must be as small as possible and the rhenium surface area must be as large as possible, and if the active component is distributed over the support in the form of a very thin outer shell.

It is an object of the present invention to find $Re_2O_7$-containing supported catalysts in which the $Re_2O_7$ component is distributed over the support in a highly disperse manner in the form of an outer shell, and which accordingly have high catalytic activities and selectivities and in particular long cycle times and service lives.

We have found that $Re_2O_7$-containing supported catalysts in which the $Re_2O_7$ component is on the inorganic support in the form of $Re_2O_7$ particles having a diameter of <1 nm, the rhenium surface area, determined by $N_2O$ pulse chemisorption, is at least 0.4 m²/g, and the $Re_2O_7$ component is distributed over the support in the form of an outer shell having a maximum thickness of 1.5 mm, can be prepared by special preparation processes.

The present invention furthermore relates to the use of the catalysts prepared in this way for olefin metathesis reactions, in particular for the conversion of $C_4$ and $C_5$ cuts, for example from steam crackers, into commercially interesting products, for example for producing propylene from $C_4$-olefins.

In particular, the present invention relates to the use of the novel catalysts for the preparation of propene by metathesis of $C_4$-olefins, as described, for example, in DE-A-196 40 026, DE-A-197 40 895 and DE-A-197 46 040.

The novel catalysts contain $Re_2O_7$ as active component applied to a support in highly disperse form. Examples of suitable supports are activated carbons, silicon carbide, aluminum oxides, silicon dioxide, titanium dioxide, zirconium dioxide, zinc oxide, magnesium oxide or mixtures thereof, preferably aluminum oxides, very particularly preferably $\gamma$-$Al_2O_3$. The supports can be, for example, in the form of tablets, extrudates or granules having diameters of, for example, from 3 mm to 5 mm. The $Re_2O_7$ content in the novel catalysts is from 1 to 50% by weight, preferably from 5 to 20% by weight, particularly preferably from 9 to 11% by weight.

The novel $Re_2O_7$-containing supported catalysts are distinguished, in particular, by the fact that the $Re_2O_7$ component is on the support in the form of $Re_2O_7$ particles having a diameter of less than 1 nm, preferably less than 0.7 nm, that the rhenium surface area—determined by $N_2O$ pulse chemisorption—is at least 0.4 m²/g, preferably at least 0.5 m²/g, and that the $Re_2O_7$ component is distributed over the support in the form of an outer shell having a maximum thickness of 1.5 mm, preferably 1.0 mm.

The size of the $Re_2O_7$ particles is determined by transmission electron microscopy. The rhenium surface area of the novel catalysts is determined with the aid of $N_2O$ pulse chemisorption. The method is described in greater detail below:

Instrument:
 Micromeritics Pulse ChemiSorb 2705.

Sample Pretreatment:
 About 1.1 g of catalyst are introduced into a quartz U-tube reactor with broadened sample part ($d_a$ corresponds to 11 mm). The sample is heated from room temperature to 400° C. at a heating rate of 80 K/min in a stream of 5% $H_2$/Ar (30 ml/min). This is followed by reduction for one hour using hydrogen 5.0 (30 ml/min) at 400° C. The sample is then eluted for 30 min in a 30 ml/min stream of He at 400° C. and cooled to 70° C. under this gas.

Performance of the Measurement
 In order to measure the relative $N_2O$ chemisorption, $N_2O$ pulses are metered into a 30 ml/min stream of helium by means of a metering loop (volume 1000 µl) and passed through the sample at 70° C. The pulses are continued until four consecutive identical pulses (equal amount of $N_2O$ in each case) are detected. The amount of $N_2O$ consumed or the $N_2$ formed is analyzed using a 0.5 m long chromatographic separating column containing Porapak-N® downstream of the reactor recorded by means of a thermal conductivity detector.

Evaluation of the Measurement:
1. The constancy of four pulses each enclosing the area $PA^i$ is used to determine the mean pulse area (MPA) in arbitrary units [a.u.]. For a total of n pulses, the following therefore applies:

$$MPA = \sum_{i=n-3}^{n} Pa^i / 4 \tag{1}$$

This value MPA can be used to convert the pulse areas into µl using the reference volume RV:

$$xMPA[\text{a.u.}] = yRV[\mu l] \tag{2}$$

2.1. The amount of adsorbed gas AG is calculated as follows from the area enclosed by the n individual pulses $PA^i$:

2.

$$AG[\text{u.a.}] = n * MPA - \sum_{i=1}^{n} PA^i = (n-4) * MPA - \sum_{i=1}^{n-4} PA^i \quad (3)$$

3. (2) is used to calculate the amount of adsorbed gas AG in $\mu l$.
4. The amount of adsorbed gas AG [$\mu l$] is converted to standard conditions $AG^s$ [$\mu l$]:

$$AG^s = AG * \frac{273 * p^m}{760 * T^m} \quad (4)$$

$p^m$=pressure [torr], $T^m$=adsorption temperature [K]
$p^m$ and $T^m$ are entered as parameters before the measurement.

5. $AG^s$ is used to calculate the first measurement parameter, the specific amount of adsorbed gas $V_m$ [cm$^3$/g] by standardization to the sample weight W.

$$V_m [\text{cm}^3/g] = \frac{AG^s [\mu l]}{1000 * W [g]} \quad (5)$$

6. Calculation of $V_m$ in [$\mu$mol/g]

$$V_m[\mu\text{ol/g}] = 44.940 * V_m[\text{cm}^3/g] \text{ for } N_2O \text{ as adsorptive.} \quad (6)$$

7. Calculation of the specific rhenium surface area $S^m$[m$^2$/g$^{cat}$]:

$$S^m [\text{m}^2/g^{cat}] = \frac{V_m [\mu\text{mol/}] * S * N_L * 10^{-6}}{K} \quad (7)$$

S=Stoichiometry factor (assumed Re=2)
K=Number of metal atoms per m$^2$ (for Re=1.54×10$^{19}$ m$^2$)
$N_L$=Avogadro's number (6.022052×10$^{23}$ mol$^{-1}$)
The novel catalysts are prepared using two special preparation processes:

Process A:

In process A, the novel catalysts are prepared by pore impregnation with a rhenium-containing solution, where the impregnation solution is heated to from 40° C. to 80° C., preferably from 50° C. to 70° C., before the impregnation. An important factor regarding the properties of the novel catalysts is that only the impregnation solution is heated to from 40° C. to 80° C., while the support is kept at room temperature. After application of the impregnation solution to the support, the impregnation solution is allowed to act on the support for a further 1 to 30 minutes, preferably from 5 to 20 minutes, before the solvent is removed by drying. The drying is carried out at from 80° C. to 170° C., preferably at from 100° C. to 150° C., for a period of from 1 to 48 hours, preferably for from 12 to 24 hours. The drying can be carried out with or without agitation.

The solvent used is preferably water. Examples of suitable rhenium precursors for this preparation variant are ammonium perrhenate, alkali metal perrhenates, aqueous perrhenic acid solution and rhenium(VII) oxide, preferably ammonium perrhenate.

Process B:

In process B, the support is introduced into a revolvable impregnation drum, which is revolved at from 2 to 100 revolutions per minute, preferably at from 5 to 20 revolutions per minute. The agitated support is sprayed with a rhenium-containing solution, where the amount of solution corresponds to the pore volume of the introduced support and the amount of solution is sprayed on over the course of 1 to 120 minutes, preferably from 5 to 60 minutes, particularly preferably from 10 to 30 minutes. After application of the impregnation solution to the support, the impregnation solution is allowed to act on the agitated support for a further 1 to a maximum of 30 minutes, preferably from 5 to 20 minutes, before the solvent is removed by drying. The drying is carried out at from 80° C. to 170° C., preferably at from 100 to 150° C., for a period of from 1 to 48 hours, preferably for from 12 to 24 hours. The drying can be carried out with or without agitation.

The solvent used is preferably water. Examples of suitable rhenium precursors for this process variant are ammonium perrhenate, alkali metal perrhenates, aqueous perrhenic acid solution and rhenium(VII) oxide, preferably aqueous perrhenic acid solution.

Before use, the novel catalysts are activated in situ by calcination at from 400 to 700° C., preferably at from 500 to 600° C.

The novel catalysts are distinguished compared with the $Re_2O_7$-containing supported catalysts known from the literature by high catalytic activities and selectivities in metathesis reactions. The novel catalysts are particularly distinguished by cycle times of at least 10 days (a cycle here is taken to mean the time in which the catalytic activity of the catalyst has dropped to half the initial activity of the catalyst at the beginning of the cycle) and by the fact that, after completion of a cycle, the catalytic activity can be restored completely, but at least to a level of 99% compared with the initial activity of the fresh catalyst, by calcination of the spent catalyst at 400–600° C. in a stream of air and cooling under an inert gas. In addition, the novel catalysts can be regenerated at least forty times, giving very long service lives of at least one year (service life=cycle time×number of cycles), which really make economical performance of metathesis processes possible.

The invention is illustrated in greater detail with reference to the following examples.

Preparation of Catalyst A:

150 g of a γ-Al$_2$O$_3$ support in the form of 4 mm extrudates having a surface area of 228 m$^2$/g and a porosity of 0.66 cm$^3$/g are impregnated with an aqueous ammonium perrhenate solution prepared by dissolving 18.5 g of ammonium perrhenate in 99 ml of water and heating to 60° C. After the impregnation solution has been applied to the support, the impregnation solution is allowed to act on the support for a further 15 minutes. The impregnated support is then immediately dried at 120° C. for 16 hours. The resultant catalyst contains 10% by weight of $Re_2O_7$. The size of the $Re_2O_7$ particles on the support surface, the rhenium surface area and the distribution of the $Re_2O_7$ component over the support are shown in Table 1.

Preparation of Catalyst B:

150 g of a γ-Al$_2$O$_3$ support in the form of 4 mm extrudates having a surface area of 228 m$^2$/g and a porosity of 0.66 cm$^3$ are introduced into an impregnation drum, which is revolved at a speed of 8 revolutions per minute. 99 ml of an aqueous perrhenic acid solution are sprayed onto the agitated support over the course of 25 minutes. The impregnation solution is then allowed to act on the agitated support for a further 5 minutes. The impregnated support is then immediately dried at 120° C. for 16 hours. The resultant catalyst contains 10% by weight of $Re_2O_7$. The size of the $Re_2O_7$ particles on the support surface, the rhenium surface area and the distribution of the $Re_2O_7$ component over the support are shown in Table 1.

Preparation of Catalyst C (comparative catalyst):

The catalyst was prepared as described in U.S. Pat. No. 4,795,734, Example 4 (column 4, lines 43–60). However, for comparability with the novel catalysts A and B, the preparation was carried out without activation at 550° C. for 3 hours and flushing with nitrogen (lines 56–60). The size of the $Re_2O_7$ particles on the support surface, the rhenium surface area and the distribution of the $Re_2O_7$ component over the support are shown in Table 1.

TABLE 1

| Catalyst | Re surface area $m^2/g$ | $Re_2O_7$ particle sizes nm | Re distribution over the support |
|---|---|---|---|
| Catalyst A | 0.63 | 0.5 | 1.5 mm thick outer shell |
| Catalyst B | 0.56 | 0.6 | 1.0 mm thick outer shell |
| Catalyst C (comparative catalyst) | 0.29 | 1.1 | homogeneous |

EXAMPLE 1a

Metathesis of an n-butene Mixture on Catalyst A

Raffinate II (40% of 1-butene, 45% of cis/trans-2-butene) was passed continuously through a tubular reactor charged with catalyst A at a reaction temperature of 60° C., a pressure of 10 bar and a space velocity of 1000 g/l*h. Before use, the catalyst was activated in situ by calcination at 550° C. The reaction product was analyzed on-line by gas chromatography. The conversion with respect to 1-butene was initially 80% and dropped over the course of 15 days to 40%, i.e. the cycle time was 15 days. The propene selectivity was 90% over the entire cycle time. When the cycle was completed, the catalyst was regenerated by calcination in a stream of air at 550° C. followed by cooling under argon. At the beginning of the second cycle, the conversion with respect to 1-butene was again 80%, i.e. the activity level of the fresh catalyst at the beginning of the first cycle was fully reached again; the propene selectivity was also 90% over the entire second cycle. In total, catalyst A could be regenerated fifty times before the initial activity no longer reached the level of at least 99% of the initial activity of the fresh catalyst, i.e. the service life was 50×15=750 days.

EXAMPLE 1b

Ethenolysis of 2-pentene on the Catalyst A

2-Pentene was passed continuously through a tubular reactor charged with catalyst A at a temperature of 40° C. and a pressure of 40 bar while ethene was metered in at a C5/C2 molar ratio of 1:1 at a space velocity of 1000 g/l×h. Before use, the catalyst was activated in situ by calcination at 550° C. The reaction product was analyzed on-line by gas chromatography. The conversion with respect to 2-pentene was initially 86% and dropped over the course of 14 days to 43%, i.e. the cycle time was 14 days. The propene selectivity was 98% over the entire cycle time. When the cycle was completed, the catalyst was regenerated by calcination in a stream of air at 550° C. followed by cooling under argon. At the beginning of the second cycle, the conversion with respect to 2-pentene was again 86%, i.e. the activity level of the fresh catalyst at the beginning of the first cycle was fully reached again; the propene selectivity was also 98% over the entire second cycle. In total, catalyst A could be regenerated forty seven times before the initial activity no longer reached the level of at least 99% of the initial activity of the fresh catalyst, i.e. the service life was 47×15=705 days.

EXAMPLE 2a

Metathesis of an n-butene Mixture on Catalyst B

Raffinate II (40% of 1-butene, 45% of cis/trans-2-butene) was passed continuously through a tubular reactor charged with catalyst B at a reaction temperature of 60° C., a pressure of 10 bar and a space velocity of 1000 g/l*h. Before use, the catalyst was activated in situ by calcination at 550° C. The reaction product was analyzed on-line by gas chromatography. The conversion with respect to 1-butene was initially 80% and dropped over the course of 15 days to 40%, i.e. the cycle time was 15 days. The propene selectivity was 90% over the entire cycle time. When the cycle was completed, the catalyst was regenerated by calcination in a stream of air at 550° C. followed by cooling under argon. At the beginning of the second cycle, the conversion with respect to 1-butene was again 80%, i.e. the activity level of the fresh catalyst at the beginning of the first cycle was fully reached again; the propene selectivity was also 90% over the entire second cycle. In total, catalyst B could be regenerated forty eight times before the initial activity no longer reached the level of at least 99% of the initial activity of the fresh catalyst, i.e. the service life was 48×15=720 days.

EXAMPLE 2b

Ethenolysis of 2-pentene on the Catalyst B

2-Pentene was passed continuously through a tubular reactor charged with catalyst B at a temperature of 40° C. and a pressure of 40 bar while ethene was metered in at a C5/C2 molar ratio of 1:1 at a space velocity of 1000 g/l×h. Before use, the catalyst was activated in situ by calcination at 550° C. The reaction product was analyzed on-line by gas chromatography. The conversion with respect to 2-pentene was initially 87% and dropped over the course of 14 days to 44%, i.e. the cycle time was 14 days. The propene selectivity was 97% over the entire cycle time. When the cycle was completed, the catalyst was regenerated by calcination in a stream of air at 550° C. followed by cooling under argon. At the beginning of the second cycle, the conversion with respect to 2-pentene was again 87%, i.e. the activity level of the fresh catalyst at the beginning of the first cycle was fully reached again; the propene selectivity was also 97% over the entire second cycle. In total, catalyst B could be regenerated forty six times before the initial activity no longer reached the level of at least 99% of the initial activity of the fresh catalyst, i.e. the service life was 46×15=690 days.

EXAMPLE 3a (comparative example)

Metathesis of an n-butene Mixture on Catalyst C (comparative catalyst)

Raffinate II (40% of 1-butene, 45% of cis/trans-2-butene) was passed continuously through a tubular reactor charged with catalyst C at a reaction temperature of 60° C., a pressure of 10 bar and a space velocity of 1000 g/l*h. Before use, the catalyst was activated in situ by calcination at 550° C. The reaction product was analyzed on-line by gas chromatography. The conversion with respect to 1-butene was initially 78% and dropped over the course of 9 days to 39%, i.e. the cycle time was only 9 days. The propene selectivity was 86% over the entire cycle time. When the cycle was completed, the catalyst was regenerated by calcination in a stream of air at 550° C. followed by cooling under argon. At the beginning of the second cycle, the conversion with respect to 1-butene was again 78%, i.e. the activity level of the fresh catalyst at the beginning of the first cycle was filly reached again; the propene selectivity was also 86% over the entire second cycle. In total, catalyst C could be regenerated thirty four times before the initial activity no longer reached the level of at least 99% of the initial activity of the fresh catalyst, i.e. the service life was 34×9=306 days.

EXAMPLE 3b (comparative example)
Ethenolysis of 2-pentene on the Catalyst C (comparative catalyst)

2-Pentene was passed continuously through a tubular reactor charged with catalyst C at a temperature of 40° C. and a pressure of 40 bar while ethene was metered in at a C5/C2 molar ratio of 1:1 at a space velocity of 1000 g/l×h. Before use, the catalyst was activated in situ by calcination at 550° C. The reaction product was analyzed on-line by gas chromatography. The conversion with respect to 2-pentene was initially 80% and dropped over the course of 8 days to 40%, i.e. the cycle time was only 8 days. The propene selectivity was 95% over the entire cycle time. When the cycle was completed, the catalyst was regenerated by calcination in a stream of air at 550° C. followed by cooling under argon. At the beginning of the second cycle, the conversion with respect to 2-pentene was again 80%, i.e. the activity level of the fresh catalyst at the beginning of the first cycle was fully reached again; the propene selectivity was also 95% over the entire second cycle. In total, catalyst C could be regenerated thirty two times before the initial activity no longer reached the level of at least 99% of the initial activity of the fresh catalyst, i.e. the service life was only 32×8=256 days.

What is claimed is:

1. A catalyst containing $Re_2O_7$ on an inorganic support, wherein the $Re_2O_7$ component is on the support in the form of $Re_2O_7$ particles having a diameter of <1 nm, the rhenium surface area, determined by $N_2O$ pulse chemisorption, is at least 0.4 m²/g, and the $Re_2O_7$ component is distributed over the support in the form of an outer shell having a maximum thickness of 1.5 mm.

2. A catalyst as claimed in claim 1, wherein the $Re_2O_7$ component is on the support in the form of $Re_2O_7$ particles having a diameter of <0.7 nm, the rhenium surface area, determined by $N_2O$ pulse chemisorption, is at least 0.5 m²/g, and the $Re_2O_7$ component is distributed over the support in the form of an outer shell having a maximum thickness of 1.0 mm.

3. A catalyst as claimed in claim 1, wherein the support is selected from the group consisting of activated carbons, silicon carbide, aluminum oxides, silicon dioxide, titanium dioxide, zirconium dioxide, zinc oxide, magnesium oxide and mixtures thereof.

4. A catalyst as claimed in claim 3, wherein the support is γ-aluminum oxide.

5. A catalyst as claimed in claim 1, wherein the $Re_2O_7$ content, based on the catalyst, is from 9 to 11% by weight.

6. A process for the preparation of a catalyst as claimed in claim 1 by impregnating the pores of a support with a rhenium-containing impregnation solution and drying the support for from 1 to 48 hours at from 80° C. to 170° C., which comprises heating exclusively the impregnation solution to from 40 to 80° C. before the impregnation, and allowing the impregnation solution to act on the support for a further 1 to 30 minutes after the impregnation.

7. A process for the preparation of a catalyst as claimed in claim 1, wherein the support is introduced into a revolvable impregnation drum, which is revolved at from 2 to 100 revolutions per minute, and sprayed with a rhenium-containing impregnation solution, where the amount of solution corresponds to the pore volume of the introduced support, the amount of solution is sprayed on over the course of 1 to 120 minutes, and the impregnation solution is allowed to act on the support for a further 1 to 30 minutes after the impregnation, and the impregnated support is dried at from 80° C. to 170° C. for from 1 to 48 hours.

8. The method of applying a catalyst as claimed in claim 1 as a metathesis catalyst.

9. The method of applying a catalyst as claimed in claim 1 for the preparation of propene by the metathesis of $C_4$-olefins.

* * * * *